United States Patent [19]

Satoh et al.

[11] Patent Number: 5,006,548
[45] Date of Patent: Apr. 9, 1991

[54] ACRYLAMIDOBENZOIC ACID DERIVATIVES AND THEIR USE

[75] Inventors: Toshio Satoh; Hitoshi Matsumoto; Hisao Kakegawa, all of Tokushima; Yoshiko Kato, Kobe; Juichi Riku, Uji; Junji Yoshinaga, Neyagawa; Yoshifumi Kanamoto, Kashihara, all of Japan

[73] Assignee: Sawai Pharmaceutical Co., Ltd., Osaka, Japan

[21] Appl. No.: 393,068

[22] Filed: Aug. 7, 1989

Related U.S. Application Data

[63] Continuation of Ser. No. 154,963, Feb. 11, 1988, abandoned, which is a continuation of Ser. No. 702,664, Feb. 19, 1985, abandoned.

[30] Foreign Application Priority Data

Feb. 29, 1984 [JP] Japan ................... 59-38971

[51] Int. Cl.$^5$ ............... A61K 31/40; A61K 31/425; A61K 31/415; C07D 339/02; C07D 333/22; C07D 207/18; C07D 231/10; C07D 233/54
[52] U.S. Cl. .................. 514/427; 514/365; 514/372; 514/385; 514/399; 514/400; 514/403; 514/406; 514/408; 514/423; 514/428; 514/438; 514/440; 514/448; 549/39; 549/71; 549/77; 548/146; 548/201; 548/204; 548/214; 548/341; 548/342; 548/378; 548/561; 548/565; 548/568
[58] Field of Search ............ 549/77, 496, 39, 71; 548/561, 341, 146, 201, 204, 214, 341, 342, 378, 565, 568; 514/438, 439, 440, 365, 372, 374, 378, 385, 403, 427, 428, 408, 399, 400, 406, 423, 448

[56] References Cited

U.S. PATENT DOCUMENTS 4,381,305 4/1983 Casagrande et al. .

FOREIGN PATENT DOCUMENTS 1235324 3/1967 Fed. Rep. of Germany .
2131843 11/1972 France .
65331 3/1970 Japan .
140413 11/1975 Japan .
65279 5/1977 Japan .
83429 7/1977 Japan .
491200 5/1980 Spain .
1298603 12/1972 United Kingdom .

OTHER PUBLICATIONS

Pharmazie, 30, HS, 76–77, 1975, by El-Kerdawy, et al.
J. Drug Res. Egypt, 7, (1), 105–110 (1975), by El-Kerdawy, et al.
Chemotherapy, 12, (5), 371–374 (1964), by Momoki, et al.
Chem. Abstract, vol. 60 2986h (1964).

Primary Examiner—Alan Siegel
Attorney, Agent, or Firm—Scully, Scott, Murphy & Presser

[57] ABSTRACT

Compounds of the general formula:

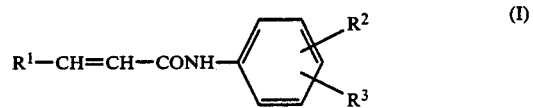

wherein $R^1$ is heterocyclic group other than pyridyl and which is unsubstituted or substituted with lower alkyl or lower alkoxycarbonyl, $R^2$ is hydrogen, halogen, or nitro, and $R^3$ is carboxy group or its functional derivative, with the proviso that when $R^1$ is an unsubstituted furyl, or furyl mono- or polysubstituted with alkyl and $R^2$ is hydrogen, then $R^3$ is functional derivative of carboxy and, where applicable, pharmaceutically acceptable salts thereof are hyaluronidase inhibitors and useful as anti-allergic agent.

14 Claims, No Drawings

ACRYLAMIDOBENZOIC ACID DERIVATIVES AND THEIR USE

This application is a continuation, of application Ser. No. 154,963, filed Feb. 11, 1988, now abandoned which is a continuation of Ser. No. 702,664, filed Feb. 19, 1985, now abandoned.

BACKGROUND OF THE INVENTION

1. Field of the Invention

The present invention relates to acrylamidobenzoic acid derivatives which have hyaluronidase-inhibiting, antiallergic and immunomodulating activities, process for preparation thereof and pharmaceutical composition comprising the said derivative.

It is well known that hyaluronidase is present in various parts of living organism normally in an inactive form and act as a phlogogenic enzyme at the inflammatory site. For example, hyaluronidase has an important role in induction of I (immediate) type allergic reaction and hence the use of hyaluronidase-inhibiting drug in these pathologic conditions appears reasonable.

On the other hand, the conventional antiallergic agents such as chlorpheniramine maleate, disodium cromoglicate, tranilast etc. have a number of deficiencies such as induction of undesirable side effect, insufficiency of peroral absorption, unsatisfactoriness of therapeutic effect and so on. Also, there has been a continuous demand for the anti-ulcerous agent which has a mechanism of action approaching the causal treatment. The inventors have succeeded in developing a antiallergic and anti-ulcerous agent which has an excellent anti-hyaluronidase activity, on the basis of a conception that hyaluronidase inhibitor is useful as a causal treatment of pathologic conditions such as a allergic disease.

2. Related Disclosures

Spanish Patent No. 491200 discloses 2-furylacrylamidobenzoic acid and 2-(mono-or polyalkyl substituted) furyl acrylamidobenzoic acid as an antiallergic agent. British Patent No. 1298603 and French Patent Publication No. 2131843 disclose 2-(pyridylacrylamido) benzoic acid and 2-pyridylvinyl-4H-3,1-benzoxazine-4-one as an intermediate for preparing 2-(pyridylvinyl)-3-tolyl-3,4-dihydroquinazolin-4-one. Japanese Patent Publication (Unexamined) Nos. 140413/1975, 65279/1977 and 83429/1977 disclose N-(3,4-dimethoxycinnamamido)anthranilic acid.

DETAILED EXPLANATION OF THE INVENTION

Summary of Invention

In one aspect, the present invention relates to a compound of the formula:

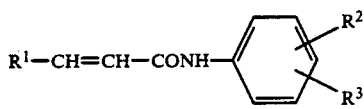

(I)

wherein $R^1$ is heterocyclic group other than pyridyl and which is unsubstituted or substituted with lower alkyl or lower alkoxycarbonyl, $R^2$ is hydrogen, halogen, or nitro, and $R^3$ is carboxy or its functional derivative, with the proviso that when $R^1$ is an unsubstituted furyl, or furyl mono- or polysubstituted with alkyl and $R^2$ is hydrogen, then $R^3$ is functional derivative of carboxy and, where applicable, pharmaceutically acceptable salts thereof.

The compound of the above formula (I) may be produced by any one of the following processes:

(a) A group $R^{3a}$ in the compound of the formula:

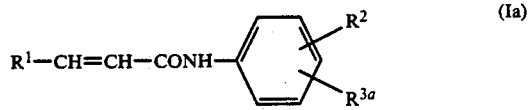

(Ia)

wherein $R^{3a}$ is functional derivative of carboxy group, and $R^1$ and $R^2$ are each as defined above, is converted into carboxy group to give a compound of the formula:

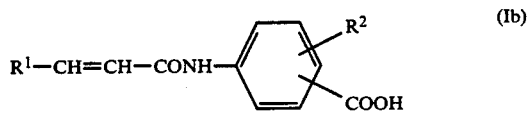

(Ib)

(b) A compound of the formula:

$R^1-CH=CH-COOH$ (II)

wherein $R^1$ is as defined above, or a reactive derivative at the carboxy group thereof is reacted with a compound of the formula:

(III)

wherein $R^2$ and $R^3$ are each as defined above, or a reactive derivative at the amino group thereof to give a compound of the formula:

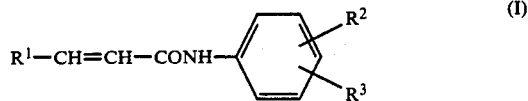

(I)

wherein $R^1$, $R^2$, and $R^3$ are each as defined above.

(c) A compound of the formula:

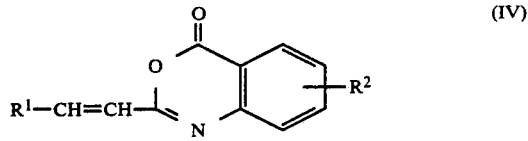

(IV)

wherein $R^1$ and $R^2$ are each as defined above, is hydrolyzed to give a compound of the formula:

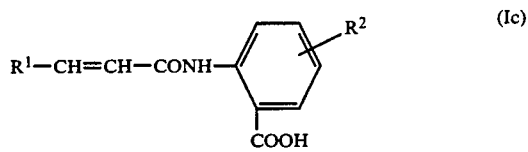

(Ic)

wherein $R^1$ and $R^2$ are each as defined above.

(d) A compound of the formula:

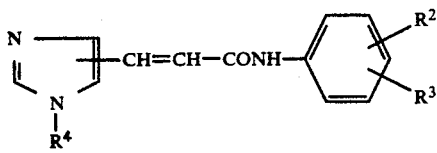

wherein $R^4$ is lower alkoxycarbonyl, and $R^2$ and $R^3$ are each as defined above, is hydrolyzed to give a compound of the formula:

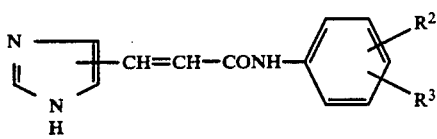

In another aspect, the present invention relates to a pharmaceutical composition useful as an antiallergic agent comprising as an active ingredient the compound of the above formula (I) or, where applicable, pharmaceutically acceptable salt thereof in association with a pharmaceutically acceptable carrier, diluent or excipient. In further aspect, the present invention relates to a pharmaceutical composition useful as a hyaluronidase inhibitor comprising as an active ingredient a compound of the formula:

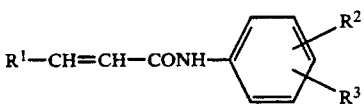

wherein $R^1$ is heterocyclic group which is unsubstituted or substituted with a lower alkyl or a lower alkoxycarbonyl, $R^2$ is hydrogen, halogen, or nitro, and $R^3$ is carboxy or its functional derivative or, where applicable, pharmaceutically acceptable salts thereof in association with a pharmaceutically acceptable carrier, diluent or excipient.

DETAILED DESCRIPTION OF THE INVENTION

The terms and the definitions described in this specification are illustrated in more detail, as follows:

The term "lower" is used to intend the group having 1 to 6 carbon atoms unless otherwise specified.

The term "heterocyclic group" for $R^1$ may include, for example, 5-membered monocyclic heterocyclic group having 1 to 4 heteroatoms selected from oxygen, nitrogen and sulfur, such as furyl, thienyl, pyrrolyl, imidazolyl, thiazolyl, triazolyl, thiadiazolyl, tetrazolyl, etc.; 6-membered monocyclic heterocyclic group having 1 to 2 heteroatoms selected from oxygen, nitrogen and sulfur, such as pyridyl, piperidyl, piperadinyl, morpholinyl, thiomorpholinyl, etc.; 7-membered monocyclic heterocyclic group such as azepinyl, diazepinyl, etc.; and condensed heterocyclic group which is consisted of the above described monocyclic heterocycle and benzene ring condensed with each other, such as indolyl, indazolyl, benzofuryl, benzothienyl, etc., of which furyl, thienyl, and pyrrolyl are preferred. The above heterocyclic groups may optionally be substituted by one or two or more (preferably from one to three) groups selected from a lower alkyl group such as methyl, ethyl, propyl, isopropyl, etc. or a lower alkoxycarbonyl group such as methoxycarbonyl, ethoxycarbonyl, tertiary butoxycarbonyl, etc. Preferable heterocyclic group is one having at least —S—, —O—, —NH— or —NY— wherein Y is lower alkyl or lower alkoxycarbonyl. The free bond of the heterocyclic group may be attached at any one of the possible positions.

The term "halogen" for $R^2$ may include fluorine, chlorine, bromine, and iodine.

The term "functional derivative" of the carboxy for $R^3$ and $R^{3a}$ may include esters and amides which are used as protective group for carboxy group as well as a compound of the formula (IV). Examples of the esters are aliphatic esters, for example, lower alkyl ester such as methyl ester, ethyl ester, propyl ester, isopropyl ester, butyl ester, t-butyl ester, pentyl ester, 1-cyclopropylethyl ester, etc., lower alkenyl ester such as vinyl ester, allyl ester, etc., lower alkynyl ester such as ethynyl ester, propynyl ester, etc., lower alkoxy (lower) alkyl ester such as methoxymethyl ester, 1-methoxyethyl ester, etc., lower alkylthio (lower) alkyl ester such as methylthiomethyl ester, ethylthiomethyl ester, etc., halo (lower) alkyl ester such as 2-iodoethyl ester, 2,2,2-trichloroethyl ester, etc., lower alkanesulfonyl (lower) alkyl ester such as mesylmethyl ester, mesylethyl ester, etc., and aromatic esters, for example, optionally substituted aryl ester such as phenyl ester, tolyl ester, t-butylphenyl ester, salicyl ester, 3,4-dimethoxyphenyl, etc., aryl (lower) alkyl ester such as benzyl ester, trityl ester, benzhydryl ester ester, etc., as well as esters with silyl compound, for example, tri (lower)alkylsilyl ester such as trimethylsilyl ester, triethylsilyl ester, etc., di (lower) alkyl (lower) alkoxysilyl ester such as dimethylmethoxysilyl ester, and diethylmethoxysilyl ester, etc. and physiologically hydrolyzable esters set forth infra.

The term "lower alkoxycarbonyl" for $R^4$ may include methoxycarbonyl, ethoxycarbonyl, tertiary butoxycarbonyl, etc.

The process for preparing the compound of the above formula (I) is explained in more detail in the following.

Process (a)

The compound of the formula (Ib) can be obtained by converting the group $R^{3a}$ in the compound of the formula (Ia) into carboxy group according to the conventional method. Any method conventionally used for removal of caryboxy-protecting group such as hydrolysis, reduction, etc. can be adopted as a method for this conversion.

The hydrolysis includes acidic hydrolysis and basic hydrolysis. Examples of acids used for acidic hydrolysis include inorganic and organic acids such as hydrochloric acid, formic acid, trifluoracetic acid, benzenesulfonic acid, cation exchanger resin, etc. Examples of bases used for basic hydrolysis include inorganic and organic bases such as alkali metal hydroxide, e.g., sodium hydroxide, potassium hydroxide, etc., alkali metal carbonate, e.g., sodium carbonate, potassium carbonate, etc., picoline, 1,5-diazabicyclo [4,3,0]-5-nonene, anion exchanger resin, etc. The hydrolysis may be carried out in a solvent, for which water, and a mixture of water and a hydrophilic organic solvent such as methanol, ethanol, tetrahydrofuran, etc. are used. The hydrolysis may also be carried out by solvolysis.

The compound of the formula (Ia) is prepared by the following process (b) described below.

Process (b)

The compound of the formula (I) can be obtained by reacting the compound (II) or a reactive derivative at the carboxy group thereof with the compound (III) or a reactive derivative at the amino group thereof according to the conventional method.

The reactive derivative at the carboxyl group of the compound (II) includes acid halides, acid anhydrides, activated esters, and activated amides. Among the acid halides, acid chloride is the most frequently used. Acid anhydrides include symmetric anhydride and mixed acid anhydrides. The latter includes, for example, dialkyl phosphoric acid mixed anhydride, dialkyl phosphorous acid mixed anhydride, alkyl carbonic acid mixed anhydride, aliphatic carboxylic acid (e.g., pivalic acid, trichloroacetic acid) mixed anhydride, etc. Active esters include methyl ester, ethyl ester, cyanomethyl ester, p-nitrophenyl ester, ester with N-hydroxysuccinimide, etc. Activated amides include amide with imidazole, dimethylimidazole, or triazol.

The reactive derivative at the amino group of the compound (III) includes Schiff's base with aldehyde (e.g., acetaldehyde, isopentanal, benzaldehyde), a reaction product with silyl compound (e.g., trimethyl silyl chloride, trimethyl silyl acetamide), a reaction product with phosphorus compound (e.g., phosphorus trichloride, phosphorus oxychloride).

In case of using the compound (II) in the form of carboxylic acid, the reaction is advantageously carried out in the presence of a condensing agent. As the condensing agent, there may be used N,N'-dicyclohexylcarbodiimide, N-cyclohexyl-N'-morpholinoethylcarbodiimide, N,N'-diisopropylcarbodiimide, N-ethylbenzisoxazolium salt, 2-chloro-1-methyl pyridinium salt, N,N'-carbonyldiimidazole, phosphorus trichloride, phosphorus oxychloride, etc.

This reaction is usually carried out in a solvent. Examples of the solvent used are dioxane, methylene chloride, tetrahydrofuran, dimethylformamide, pyridine, benzene, toluene, xylene, etc.

A preferred example of operation is as follows: 2-Chloro-1-methylpyridinium iodide is suspended in dry methylene chloride under nitrogen stream. A solution of the compounds (II) and (III) and triethylamine in dry methylene chloride is added dropwise, and the mixture is heated under reflux for 18 to 40 hours. Alternatively, the compound (III) is dissolved in dry dioxane, and chloride of the compound (II) is added dropwise at room temperature. The mixture is stirred overnight.

The compounds (II) and (III) are either the known compounds commercially available or those producible in a similar manner to that of the known compounds.

Process (c)

The compound (Ic) can be obtained by hydrolyzing the compound (IV).

The hydrolysis is carried out in water or an aqueous solvent (e.g., aqueous alcohol such as water-containing methanol, water-containing ethanol, etc.), with addition of an acid or a base as necessary. Suitable reaction temperature is room temperature or an elevated temperature.

An example of the preferred operating method is shown, as follows: To the compound (IV) NaOH in 7-times the molar amount to the former is added, and the mixture is heated. When the temperature reaches 70° C., methanol is added, and the mixture is allowed to react for 1 hour. After removing the solvent (mainly methanol) under reduced pressure, the residue is acidified (pH about 4) with 10% HCl to precipitate the compound (Ic) as white solid.

The compound (IV) is obtainable by condensing aldehyde $R^1$—CHO(VI) with the compound (V):

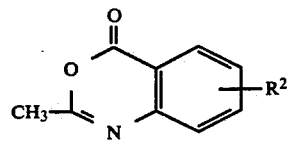

wherein $R^1$ and $R^2$ are each as defined above. This reaction may be effected by heating without solvent, or preferably effected by heating in the presence of a water-eliminating condensing agent such as Lewis acid (e.g., $BF_3$, $ZnCl_2$, $TiCl_4$, $AlCl_3$, etc.) in an inert solvent. To show a preferred example of operation, the compound (V) is dissolved in dry toluene, and 1.5 times the molar amount of the compound (VI) and 0.1 times the molar amount of $BF_3.(C_2H_5)_2O$ relative to 1 molar amount of the compound (V) are added. The mixture is heated under reflux in a nitrogen stream for 24 hours and filtered while hot. The solvent is removed, and toluene is added to the residue to precipitate the compound (IV). From the mother liquor, also the compound (IV) is obtained by chromatography. The compound (IV) obtainable by this process is mainly in a trans-form.

The compound (V) is prepared in accordance with the process described in Journal of Organic Chemistry, 41, 1763 (1976).

Process (d)

The compound (Ie) can be obtained by hydrolyzing the compound (Id).

This hydrolysis is carried out in the same manner as that described in Process (a).

The compound (Id) is prepared, for example, by the process (b).

In carrying out the hydrolysis (a), (c), or (d) above, when the starting compound contains a group which is easily hydrolyzable, it may occur that the said group is simultaneously hydrolyzed, but, as far as the product is a compound included in the formula (I), it is to be appreciated that such a case is to be included in the present invention. Thus, where, for instance, $R^1$ of the starting compound is N-lower alkoxycarbonylimidazolyl group and $R^3$ is a derivative of carboxyl group ($R^{3a}$), it is possible to operate the processes (a) and (d) simultaneously.

When the group $R^3$ in the compound (I) or (I') is carboxy, any salts of such compound are also included within the scope of the invention. Examples of the salts include those with alkali metals such as sodium, potassium etc., alkali earth metals such as calucium, magnesium etc., other metals such as aluminum, organic amines such as ethanolamine, diethanolamine, pyrrolidine, piperidine, morpholine, N-methylpiperazine, N-hydroxyethylpiperazine, and amino acids such as lysine, arginine, ornitine, histidine, etc. These salts can be obtained by reacting the appropriate free carboxylic acid with the appropriate base.

In the compound (I) or (I') having carboxy group as $R^3$, when said compound is not satisfactory in property such as solubility, stability, absorbability etc., a modified compound having improved properties may be obtained by converting the carboxy group in the original compound into a pharmaceutically acceptable derivative (i.e. bioprecursor). Such improved compound, when administered, is converted into the original carboxy compound in the body. Examples of these compound include those having pharmaceutically acceptable, physiologically hydrolyzable ester as $R^3$. The esters include methyl ester, ethyl ester, isopropyl ester, tert-butyl ester, acetoxymethyl ester, 1-(ethoxycarbonyloxy)ethyl ester, pivaloyloxymethyl ester, phthalidyl ester, 5-indanyl ester, 2-(3-phthalidylidene)ethyl ester, (5-methyl-2-oxo-1,3-dioxole-4-yl)methyl ester etc.

The compound (I') has been shown to have hyaluronidase inhibiting action and accordingly is useful as medicine. Also, the compound (I) has been shown to have anti-allergic action and accordingly is useful as medicine. Preferable compounds are those wherein the group $R^3$ is attached at ortho position to the carbamoyl (—CONH—) group. Further, these compounds have an advantage of low toxicity.

For the above usages, the required dose will, of course, vary depending on the compound used, mode of administration, and treatment desired. In general, satisfactory results are obtainable in administration at a dosage of 1 to 6 mg/kg conveniently administered in division in two to four divided dosages a day or in sustained release form.

For prophylactic and/or therapeutic administration, the compound according to the invention can be used in a form of conventional pharmaceutical preparation which contains the said compound, as an active ingredient, in admixture with a pharmaceutically acceptable carrier such as organic or inorganic, solid or liquid excipients suitable for peroral administration, parenteral or external application. Such preparation may be in a solid form such as capsule, tablet, sugar-coated tablet, ointment, suppository, etc. or in a liquid form such as solution, suspension, emulsion, etc. The above preparation may also contain auxiliary substance, stabilizer, humectant, emulsifier, buffer, and other conventional additives.

The present invention is illustrated in more detail by way of the following Examples and Test Examples. In the following experiments, Art 5735 made by Merck was used as silica gel for TLC, and Art 7734 made by Merck as silica gel for column.

PREPARATION 1

Preparation of
2-[2-(3-thienyl)vinyl]-4H-3,1-benzoxazine-4-one

2-Methyl-4H-3,1-benzoxazine-4-one (2 g, 12.4 mmol) was dissolved in dry toluene (37 ml), and 3-thiophenecarboxaldehyde (1.66 ml, 18.6 mmol) and boron trifluoride etherate (0.16 ml, 1.24 mmol) were added. The mixture was heated under reflux in nitrogen stream for 24 hours. The reaction mixture was filtered while hot and the solvent was removed from the filtrate. To the residue solidified on removal of solvent was added toluene (10 ml) and the insoluble matter was collected on filter (728 mg). The filtrate was adsorbed on a silica gel column and the desired compound was separated. (developing solvent: ethyl acetate:n-hexane=1:1). The solvent was removed from the yellow eluate of the desired compound which flowed out for the first time to give pale yellow solid (1.821 g). On combining with the first solid, 2.549 g of the desired compound was obtained (yield, 80.5%). Recrystallization from methanol/tetrahydrofuran gave the purified crystals (1.707 g). m.p., 130°–131° C.

In a similar manner, the compounds shown in the following table were obtained. The mark ** shows the melting point of the crude crystals isolated freeing from the column.

TABLE

| $R^1$ | $R^2$ | mp(°C.) | Yield (%) | IR(KBr, cm$^{-1}$) |
|---|---|---|---|---|
| 3-thienyl | H | 130–131 | 80.5 | 1750 C(=O)—O— |
| 2-thienyl | H | 149–151 | 76 | 1760 C(=O)—O— |
| 2-furyl | H | 131–135 | 29 | 1755 C(=O)—O— |
| 2-furyl | 7-Cl | 190–193** | 34 | 1750 C(=O)—O— |
| 2-furyl | 7-NO$_2$ | 175–178** | 20 | 1745 C(=O)—O— |
| 1-methyl-2-pyrrolyl | H | 182–184 | 18 | 1750 C(=O)—O— |

PREPARATION 2

Preparation of
4-bromomethyl-5-methyl-1,3-dioxole-2-one

According to the method described in Liebigs. Ann. Chem., 1977, 27–32 4,5-dimethyl-1,3-dioxole-2-one (500 mg, 4.38 mmol) and N-bromosuccinimide (0.78 g, 4.38 mmol) were heated under reflux in dry carbon tetrachloride in the presence of α-α'-azobisisobutyronitrile (7.5 mg) for 20 minutes.

The reaction mixture was concentrated under reduced pressure to half the volume, and the precipitated solid was filtered by suction. After removing the solvent from the filtrate, the residue was analyzed by gas chromatography. The obtained mixture (792 mg), contained 70% of the desired title compound and used for the subsequent reactions.

EXAMPLE 1

Preparation of 2-[3-(2-thienyl)acrylamido]benzoic acid (Compound 2) (Process a)

Ethyl 2-[3-(2-thienyl)acrylamido]benzoate (150 mg, 0.50 mmol) prepared in Example 2 was dissolved in methanol (3 ml) while warming, and 1N-aqueous NaOH (1.8 ml, 1.80 mmol) was added dropwide under stirring. The mixture was stirred at 70° C. for 1 hour. After the reaction, methanol was removed, and the residue was treated with water under ice cooling and acidified (to pH 4) with 10% HCl. The precipitated solid were collected on a filter, washed with water, and dried to give white solids of the title compound (125 mg, yield, 92%), which were recrystallized from the mixed solvent of methanol and water. m.p., 215°–216° C.

IR (KBr, cm$^{-1}$): 3300–2500, 1695, 1650 (COOH or —CONH—)

$^1$H-NMR (DMSO-d$_6$, δ): 11.5 (s, 1H, —CONHH—), 8.7—6.4 (m, aromatic hydrogen)

EXAMPLE 2

Preparation of ethyl
2-[3-(2-thienyl)acrylamido]benzoate (Process b)

Under nitrogen stream, 2-chloro-1-methylpyridinium iodide (966 mg, 3.89 mmol) was suspended in dry methylene chloride (5 ml). To the suspension, a solution of 3-(2-thienyl)acrylic acid (500 mg, 3.24 mmol), triethylamine (1.08 ml, 7.78 mmol), and ethyl 2-aminobenzoate (0.48 ml, 3.24 mmol) in dry methylene chloride (5 ml)

was added dropwise. After the addition, the mixture was heated under reflux for 39 hours. Then, the reaction mixture was diluted with methylene chloride, washed with 10% aqueous HCl, saturated aqueous sodium chloride, 1N-aqueous NaOH, and saturated aqueous sodium chloride successively, and dried. Removal of solvent gave a yellow solid, which was washed with n-hexane to give pale yellow solids of the title compound (442 mg, yield, 45%). m.p., 126°–127° C. (recrystallized from methanol)

IR (KBr, cm$^{-1}$): 3200 (CONH), 1695 (COOR), 1670 (—NHCO—)

$^1$H-NMR (DMSO-d$_6$, δ: 11.5 (s, 1H, —NHCO—)

EXAMPLE 3

Preparation of methyl 2-[3-(1-tertiary butoxycarbonyl-1H-imidazole-4-yl)acrylamido]benzoate (Process b)

N-t-butoxycarbonylurocanic acid [prepared from urocanic acid and di-t-butyl dicarbonate; cf. U.S. Pat. No. 4,313,948] (2.5 g, 10.50 mmol), triethylamine (2.55 g, 25.20 mmol), and 2-chloro-1-methylpyridinium iodide (3.129 g, 12.60 mmol) were stirred in dry methylene chloride under nitrogen stream at room temperature for 1 hour. The methyl 2-aminobenzoate (1.587 g, 10.50 mmol) was added and the mixture was refluxed at 40° C. for 18 hours. The title compound was separated directly by preparative TLC using silica gel [developing solvent: ethyl acetate:benzene=1:4]. The silica gel was extracted with solvent, and after removal of the solvent, the residue was crystallized by treating with isopropylether to give white solids of the title compound (190 mg, yield, 7%). m.p., 156°–157° C.

Rf: 0.22 (ethyl acetate:benzene=1:4)

IR (KBr, cm$^{-1}$): 3300 (—CONH—), 1750 (—COOC(CH$_3$)$_3$), 1680 and 1640 (COOCH$_3$ or CONH)

$^1$H-NMR (CDCl$_3$, δ): 11.40 (s, 1H, —NHCO—), 3.90 (s, 3H, —COOCH$_3$), 1.60 (s, 9H, —COOC(CH$_3$)$_3$)

EXAMPLE 4

Preparation of 2-[3-(3-thienyl)acrylamido]benzoic acid (Compound 1) (Process c)

To 2-[2-(3-thienyl)vinyl]-4H-3,1-benzoxazine-4-one (800 mg, 3.13 mmol) was added 1N-NaOH (21.9 ml) and the mixture was heated to 70° C. After adding methanol (30 ml), and the mixture was reacted for 1 hour. The methanol was removed from the reaction mixture under reduced pressure, and the residue was acidified with 10% HCl under cooling (pH about 4) to give a white solid, which was collected on a filter, washed with water, and dried to give the title compound (826 mg, yield, 96%). m.p., 218°–219° C.

IR (KBr, cm$^{-1}$): 1701, 1660 (—COOH or —NHCO—)

$^1$H-NMR (DMSO-d$_6$, ): 11.45 (s, 1H, —CONH—)

EXAMPLE 5

Preparation of 2-[3-(1H-imidazole-4-yl)acrylamido]benzoic acid (Compound 7) (Process a or d)

Methyl 2-[3-(1-t-butoxycarbonyl-1H-imidazole-4-yl)acrylamido]benzoate (168 mg) was dissolved in methanol (9 ml), 3N.HCl (2 ml) was added. The mixture was stirred at room temperature for 1 hour. Then, methanol was removed and the precipitated solid were filtered. The solid were again dissolved in methanol (9 ml), and 1N-NaOH (0.9 ml) was added. The mixture was reacted with stirring at 70° C. for 1 hour. After removing methanol, the mixture was treated with water and slightly acidified by KHSO$_4$ under ice cooling to give white solids of the title compound (88 mg, yield, 76%). m.p., 263°–265° C.

IR (KBr, cm$^{-1}$): 1670, 1630 (—COOH or —NHCO—)

EXAMPLE 6

Preparation of ethyl 2-[3-(2-furyl)acrylamido]benzoate (Process b)

Under nitrogen stream, 2-chloro-1-methylpyridinium iodide (1.272 g, 4.34 mmol) was suspended in dry methylene chloride (5 ml). To the suspension a solution of 3-(2-furyl)acrylic acid (500 mg, 3.62 mmol), triethylamine (1.2 ml, 8.69 mmol), and ethyl 2-aminobenzoate (0.53 ml, 3.62 mmol) in dry methylene chloride (5 ml) was added. The mixture was heated under reflux for 40 hours. Then, the reaction mixture was diluted with methylene chloride, and washed with 10% aqueous HCl, saturated aqueous sodium chloride, 1N-aqueous NaOH, and saturated aqueous sodium chloride successively, and dried. Removal of solvent gave a viscous oil, which, on washing with n-hexane gave white solids of the title compound (312 mg, yield: 30.2%), which was recrystallized from methanol. m.p., 85°–86° C.

Rf: 0.40 (ether:n-hexane=2:3)

IR (KBr, cm$^{-1}$): 3250 (CONH), 1695 (COOC$_2$H$_5$), 1680 (CONH)

$^1$H-NMR (CDCl$_3$, δ): 11.4 (s, 1H, CONH), 8.9–6.4 (m, aromatic hydrogen), 4.4 (q, 2H, —COOCH$_2$CH$_3$), 1.4 (t, 3H, —COOCH$_2$CH$_3$)

By using the processes of the above examples, the compounds as shown in the following table were obtained. The processes are shown by the Numbers of Example in which the compounds were actually produced or in which similar reaction systems were used. The mark * shows the yield after recrystallization.

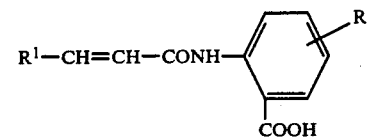

| Compound | Example | R$^1$ | R$^2$ | mp (°C.) | Yield |
|---|---|---|---|---|---|
| 1 | 1,2,4 | 3-thienyl | H | 218–219 | 96 |
| 2 | 1,2,4 | 2-thienyl | H | 215–216 | 92 |
| 3 | 1,2,4,6 | 2-furyl | H | 184–186 | 88 |
| 4 | 1,2,4 | 2-furyl | Cl | 205–207 | 25* |
| 5 | 1,2,4 | 2-furyl | NO$_2$ | 220–222 | 44* |
| 6 | 1,2,4 | 1-methyl-2-pyrrolyl | H | 181–184 | 48* |
| 7 | 2,3,5 | 4-imidazolyl | H | 263–265 | 76 |

EXAMPLE 7

Sodium 2-[3-(2-thienyl)acrylamido]benzoate

To a slution of 2-[3-(2-thienyl)acrylamido]benzoic acid (546 mg, 2 mmol) in methanol (2 ml) was added 1N-aqueous NaOH (2 ml), and the mixture was stirred at room temperature for 3 hours. The reaction mixture was filtered by suction, and after removing the solvent from the filtrate, the residue was sufficiently washed with ethyl acetate to give pale yellow solids of the desired sodium salt (442 mg, yield 75%). m.p., 204°–210° C.

IR (KBr, cm$^{-1}$): 3400 (br), 1640, 1580, 1495
$^1$H-NMR (DMSO-d$_6$, δ): 14.59 (s, 1H, —CONH—), 6.20–8.73 (m, 9H, aromatic hydrogen, vinyl hydrogen)

EXAMPLE 8

Potassium 2-[3-(2-thienyl)acrylamido]benzoate

To a solution of 2-[3-(2-thienyl)acrylamido]benzoic acid (546 mg, 2 mmol) in acetone (20 ml) were added potassium carbonate (138 mg, 1 mmol) and water (10 ml), and the mixture was stirred at room temperature for 1 hour.

After the reaction, the solvent was removed. The residue was treated with distilled water, filtered by suction, and the solvent was removed from the filtrate. The residue was washed with ethyl acetate to give pale yellow solids of the desired potassium salt (472 mg, yield, 76%). m.p., 222°–225° C. (decomposition)

IR (KBr, cm$^{-1}$: 3500 (br), 3100 (br), 1650, 1600, 1580
$^1$H-NMR (DMSO-d$_6$, δ): 14.90 (s, 1H, —CONH—), 6.16–8.66 (m, 9H, aromatic hydrogen, vinyl hydrogen)

EXAMPLE 9

Calcium 2-[3-(2-thienyl)acrylamindo]benzoate

To a solution of 2-[3-(2-thienyl)acrylamindo]benzoic acid (546 mg, 2 mmol) in tetrahydrofuran (20 ml) were added calcium carbonate (100 mg, 1 mmol) and water (10 ml). The mixture was stirred at room temperature for 24 hours.

The reaction mixture was filtered by suction, and the solvent was removed from the filtrate. The residue was washed with ethyl acetate to give pale yellow solids of the desired calcium salt (512 mg, yield, 87%). m.p., 279°–286° C.

IR (KBr, cm$^{-1}$): 3450 (br), 3000 (br), 1650, 1600, 1580
$^1$H-NMR (DMSO-d$_6$, δ): 14.70 (s, 1H, —CONH—), 6.16–8.73 (m, 9H, aromatic hydrogen, vinyl hyarogen)

EXAMPLE 10

2-[3-(2-thienyl)acrylamido]benzoic acid L-lysine salt

To a solution of 2-[3-(2-thienyl)acrylamido]benzoic acid (500 mg, 1.8 mmol) in tetrahydrofuran (5 ml) was added L-lysine (267 mg, 1.8 mmol) dissolved in water (3 ml). After stirring the mixture at room temperature for 1.5 hour, the solvent was removed, and the residue was triturated with ether to give crystals. After filtering and drying, the crystals were dissolved in water, the insoluble matter was removed and water was distilled off. The residue was crystallized with ether to give pale yellow solids of the desired L-lysine salt (510 mg, yield, 66%). m.p., 208°–213° C.

IR (KBr, cm$^{-1}$): 3700–2200, 1580
$^1$H-NMR (DMSO-d$_6$, δ): 14.22 (s, 1H, —CONH—), 6.18–8.63 (m, 9H, aromatic hydrogen, vinyl hydrogen), 3.40 (br), 2.83 (br), 1.60 (br).

EXAMPLE 11

2-[3-(2-thienyl)acrylamido]benzoic acid L-arginine salt

To a solution of 2-[3-(2-thienyl)acrylamido]benzoic acid (500 mg, 1.8 mmol) in tetrahydrofuran (5 ml) was added L-arginine (319 mg, 1.8 mmol) dissolved in water (3 ml). After stirring the mixture at room temperature for 1.5 hour, the solvent was removed, and the residue was triturated with ether to give crystals.

After filtration and drying, the crystals were dissolved in water, insoluble matter was filtered, and water was distilled off. The residue was crystallized with ether to give pale yellow solids of the desired L-arginine salt (573 mg, yield, 70%). m.p., 155°–159° C.

IR (KBr, cm$^{-1}$): 3700–2200, 1640 (br), 1580
$^1$H-NMR (DMSO-d$_6$, δ): 14.05 (s, 1H, —CONH—), 8.58–6.15 (m, aromatic hydrogen, vinyl hydrogen), 3.42, 3.15, 1.77 (br)

EXAMPLE 12

Pivaloyloxymethyl 2-[3-(2-thienyl)acrylamido]benzoate

A mixture of 2-[3-(2-thienyl)acrylamido]benzoic acid (273 mg, 1 mmol) and triethylamine (0.2 ml, 1.4 mmol) in dry acetone (10 ml) was stirred at room temperature for 30 minutes. The resulting solution was treated with chloromethyl pivalate (0.21 ml, 1.4 mmol) and sodium iodide (210 mg, 1.4 mmol), and the mixture was heated under reflux for 1 hour. The reaction mixture was filtered by suction, and the solvent was removed from the filtrate.

The residue was dissolved in chloroform and washed with saturated aqueous sodium hydrogen carbonate, then with saturated aqueous sodium chloride, and dried over magnesium sulfate. After removing the solvent, the resulting solid was recrystallized from the mixed solvent of methanol and water to give white crystals of the desired compound (289 mg, yield, 75%). m.p., 125°–126° C.

IR (KBr, cm$^{-1}$): 3300, 1750, 1700, 1685
$^1$H-NMR (CDCl$_3$, δ): 1.21 (s, 9H, —C(CH$_3$)$_3$), 5.98 (s, 2H, —COOCH$_2$OCOC(CH$_3$)$_3$), 6.38 (d, 1H, —CH═CH—), 6.88–8.15 (m, 7H, aromatic hydrogen, vinyl hydrogen), 8.78 (d, 1H, aromatic hydrogen), 11.10 (brs, 1H, —CONH—)

EXAMPLE 13

Methyl 2-[3-(2-thienyl)acrylamido]benzoate

To a suspension of 2-[3-(2-thienyl)acrylamido]benzoic acid (273 mg, 1 mmol) in dry acetone (2 ml) were added potassium carbonate (194 mg, 1.4 mmol) and dry dimethylformamide (1 ml). The mixture was treated with methyl iodide (199 mg, 1.4 mmol) and dry dimethylformamide (2 ml) and stirred at room temperature for 3 hours. The reaction mixture was poured into ice water, the precipitated solid was collected on a filter by suction, dried, and recrystallized from the mixed solvent of methanol and water to give pale yellow crystals of the desired compound (213 mg, yield, 74%). m.p., 126°–127° C.

IR (KBr, cm$^{-1}$): 3250, 1685, 1670
$^1$H-NMR (CDCl$_3$, δ): 3.92 (s, 3H, —CH$_3$), 6.22–8.13 (m, 8H, aromatic hydrogen, vinyl hydrogen), 8.80 (d, 1H, aromatic hydrogen), 11.38 (brs, 1H, —CONH—)

EXAMPLE 14

Ethyl 2-[3-(2-thienyl)acrylamido]benzoate

To a suspension of 2-[3-(2-thienyl)acrylamido]benzoic acid (273 mg, 1 mmol) in acetone (2 ml) were added potassium carbonate (194 mg, 1.4 mmol) and dry dimethylformamide (1 ml). To the resulting solution, ethyl iodide (218 mg, 1.4 mmol) and dry dimethylformamide (2 ml) were added and the mixture was stirred at 60° C. for 1 hour. The reaction mixture was poured into ice water. The precipitated solid was collected by suction, and recrystallized from methanol to give pale yellow crystals of the desired compound (197 mg, yield, 65%). m.p., 120°–122° C.

IR (KBr, cm$^{-1}$): 3150, 1690, 1670

¹H-NMR (CDCl₃, δ): 1.43 (t, 3H, —CH₂C$\underline{H_3}$), 4.40 (q, 2H, —C$\underline{H_2}$CH₃), 6.20–8.17 (m, 8H, aromatic hydrogen, vinyl hydrogen), 8.83 (d, 1H, aromatic hydrogen), 11.43 (brs, 1H, —CON$\underline{H}$—)

EXAMPLE 15

1,3-Dihydro-3-oxo-1-isobenzofuranyl 2-[3-(2-thienyl)acrylamido]benzoate

A mixture of 2-[3-(2-thienyl)acrylamido]benzoic acid (273 mg, 1 mmol) and triethylamine (0.14 ml, 1 mmol) in dry acetone (10 ml) was stirred at room temperature for 30 minutes. A solution of 3-bromophtalide (213 mg, 1 mmol) in acetone (2 ml) was added under ice cooling, and the mixture was stirred at room temperature for 23 hours. The reaction mixture was filtered by suction, and the solvent was removed from the filtrate. The residue was dissolved in chloroform, washed with saturated aqueous sodium hydrogen carbonate, then with saturated aqueous sodium chloride, and dried over magnesium sulfate. The solvent was removed and the residue was purified by silica gel column chromatography (developing solvent: benzene:ether=49:1). The pale yellow second eluate was collected. After removing the solvent, the resulting oily product was crystallized with isopropyl ether to give the desired compound (159 mg, yield, 39%). m.p., 194°–195° C. (white crystals, recrystallized from benzene-n-hexane)

IR (KBr, cm⁻¹): 3350, 1785, 1710, 1670

¹H-NMR (CDCl₃, δ): 6.23–8.13 (m, 13H, aromatic hydrogen, vinyl hydrogen), 8.85 (d, 1H, aromatic hydrogen), 11.07 (brs, 1H, —CON$\underline{H}$—)

EXAMPLE 16

1-[(Ethoxycarbonyl)oxy]ethyl 2-[3-(2-thienyl)acrylamido]benzoate

A mixture of 2-[3-(2-thienyl)acrylamido]benzoic acid (273 mg, 1 mmol) and triethylamine (0.2 ml, 1.4 mmol) in dry acetone (10 ml) was stirred at room temperature for 30 minutes. To the solution, 1-chloroethyl ethyl carbonate (214 mg, 1.4 mmol) and sodium iodide (210 mg, 1.4 mmol) were added under ice cooling, and the mixture was heated under reflux for 19 hours. The reaction mixture was filtered by suction and the solvent was removed from the filtrate. The residue was dissolved in chloroform, washed with saturated aqueous sodium hydrogen carbonate, then with saturated aqueous sodium chloride, and dried over magnesium sulfate. After removing the solvent, the residue was purified by silica gel column chromatography (developing solvent:benzene:ether=49:1). The second eluate was collected. After removing the solvent, the resulted oily product was crystallized with isopropyl ether to give the desired compound (98 mg, yield, 25%). m.p., 154°–156° C. (white crystals, recrystallized from methanol/tetrahydrofuran/water).

IR (KBr, cm⁻¹): 3250, 1755, 1690 (shoulder), 1670

¹H-NMR (CDCl₃, δ): 1.32 (t, 3H, —CH₂C$\underline{H_3}$), 1.67 (d, 3H, —CH(C$\underline{H_3}$)—), 4.23 (q, 2H, —C$\underline{H_2}$CH₃), 6.17–8.17 (m, 9H, aromatic hydrogen, vinyl hydrogen, —C$\underline{H}$(CH₃)—), 8.83 (d, 1H, aromatic hydrogen), 11.13 (brs, 1$\underline{H}$, —CON$\underline{H}$—)

EXAMPLE 17

T-butyl 2-[3-(2-thienyl)acrylamido]benzoate

To a solution of 2-(2-(2-thienyl)vinyl)-4H-3,1-benzoxazine-4-one (500 mg, 1.95 mmol) in dry benzene (40 ml) was added potassium t-butoxide (306 mg, 2.72 mmol), and the mixture was heated under reflux for 2 hours. The solvent was removed from the reaction mixture. The residue was extracted with chloroform, washed with 0.5N-HCl, then with saturated aqueous sodium chloride, and dried over magnesium sulfate.

After removing the solvent, the residue was purified by column chromatography (developing solvent:benzene:ethyl acetate=4:1) to give pale yellow crystals of the desired compound (260 mg, yield, 40%). m.p., 113°–116° C. (methanol/water)

IR (KBr, cm⁻¹): 3220, 1660

¹H-NMR (CDCl₃, δ): 1.70 (s, 9H, —C(CH₃)₃), 8.95–6.35 (m, 9H, aromatic hydrogen, vinyl hydrogen), 11.6 (s, 1H, —CON$\underline{H}$—)

EXAMPLE 18

Pivaloyloxy methyl 2-[3-(2-furyl)acrylamido]benzoate

A mixture of 2-[3-(2-furyl)acrylamido]benzoic acid (257 mg, 1 mmol) and triethylamine (0.2 ml, 1.4 mmol) in dry acetone (10 ml) was stirred at room temperature for 30 minutes. To the resulting solution, chloromethyl pivalate (0.21 ml, 1.4 mmol) and sodium iodide (210 mg, 1.4 mmol) were added, and the mixture was heated under reflux for 3 hours. The reaction mixture was filtered by suction, and the solvent was removed from the filtrate. The residue was dissolved in chloroform, washed with saturated aqueous sodium hydrogen carbonate, then with saturated aqueous sodium chloride, and dried over magnesium sulfate.

After removing the solvent, the residue was purified by column chromatography (developing solvent:benzene:ether=9:1). The colorless solution which eluted first was collected. The solvent was removed to give pale yellow crystals of the desired compound (320 mg, yield, 86%). m.p., 120°–122° C. (methanol/water)

IR (KBr, cm⁻¹): 3280, 1750, 1700, 1685

¹H-NMR (CDCl₃, δ): 1.25 (s, 9H, —C(CH₃)₃), 5.98 (s, 2H, —COOC$\underline{H_2}$OC(O)—), 6.33–8.20 (m, $\overline{8H}$, aromatic hydrogen, vinyl hydrogen), 8.83 (d, 1H, aromatic hydrogen), 11.00 (brs, 1H, —CON$\underline{H}$—)

EXAMPLE 19

5-Methyl-2-oxo-1,3-dioxole-4-ylmethyl 2-[3-(2-thienyl)acrylamido]benzoate

A mixture of 2-[3-(2-thienyl)acrylamido]benzoic acid (273 mg, 1 mmol) and triethylamine (0.2 ml, 1.4 mmol) in dry acetone (10 ml) was stirred at room temperature for 30 minutes.

To the resulting solution, a solution of 4-bromomethyl-5-methyl-1,3-dioxole-2-one (386 mg, 1.4 mmol) in dry acetone (2 ml) was added under ice cooling, and the mixture was heated under reflux for 2.5 hours. The reaction mixture was filtered by suction, and the solvent was removed from the filtrate. The residue was dissolved in chloroform, washed with saturated aqueous sodium hydrogen carbonate, then with saturated aqueous sodium chloride, and dried over magnesium sulfate.

After removing the solvent, the residue was purified by column chromatography (developing solvent: benzene:ether=9:1). The pale yellow second eluate was collected. After removing the solvent, the resulting oily product was crystallized with isopropyl ether to give the desired compound (227 mg, yield, 59%). m.p., 139°–140° C. (methanol)

IR (KBr, cm⁻¹): 3250, 1860, 1830, 1730, 1690 (shoulder), 1670

$^1$H-NMR (CDCl$_3$, δ): 2.23 (s, 3H, C$\underline{H}_3$), 5.10 (s, 2H, —OC$\underline{H}_2$—), 6.20–8.13 (m, 8H, aromatic hydrogen, vinyl hydrogen), 8.80 (d, 1H, aromatic hydrogen), 10.90 (brs, 1H, —CON$\underline{H}$)

EXAMPLE 20

5-Methyl-2-oxo-1,3-dioxole-4-ylmethyl 2-[3-(2-furyl)acrylamido]benzoate

A mixture of 2-[3-(2-furyl)acrylamido]benzoic acid (257 mg, 1 mmol) and triethylamine (0.2 ml, 1.4 mmol) in dry acetone (10 ml) was stirred at room temperature for 30 minutes.

To the resulting solution, a solution of 4-bromomethyl-5-methyl-1,3-dioxole-2-one (386 mg, 1.4 mmol) in dry acetone (2 ml) was added under ice cooling, and the mixture was heated under reflux for 1 hour. The reaction mixture was filtered by suction, and the solvent was removed from the filtrate. The residue was dissolved in chloroform, washed with saturated aqueous sodium hydrogen carbonate, then with saturated aqueous sodium chloride, and dried over magnesium sulfate.

After removing the solvent, the residue was purified by column chromatography (developing solvent: benzene: ether=9:1). The pale yellow second eluate was collected. After removing the solvent, the resulting oily product was crystallized with isopropyl ether to give the desired compound (292 mg, yield, 79%). m.p., 142°–143.5° C. (methanol).

IR (KBr, cm$^{-1}$): 3400, 1820, 1740, 1680 (shoulder), 1670

$^1$H-NMR (CDCl$_3$, δ): 2.23 (s, 3H, C$\underline{H}_3$), 5.10 (s, 2H, —OC$\underline{H}_2$—), 6.33–8.17 (m, 8H, aromatic hydrogen, vinyl hydrogen), 8.83 (d, 1H, aromatic hydrogen), 11.13 (brs, 1H, —CON$\underline{H}$)

EXAMPLE 21

| (1) Active ingredient | 25.00 mg |
|---|---|
| (2) Lactose | 49.00 mg |
| Crystal cellulose | 36.00 mg |
| Corn starch | 5.00 mg |
| (3) Hydroxypropyl cellulose | 1.00 mg |
| (4) ECG505 (Carboxymethyl cellulose calcium) | 2.00 mg |
| (5) Magnesium stearate | 1.00 mg |
| (6) Talc | 1.00 mg |
| Total | 120 mg |

(1)+(2) was kneaded with a 5% aqueous solution of (3), granulated, and mixed with (4), (5), and (6). The resultant mixture was pressed into tablets (120 mg/tablet, 7 mm in diameter).

EXAMPLE 22

| (1) Active ingredient | 50.00 mg |
|---|---|
| (2) Lactose | 124.50 mg |
| (3) Corn starch | 20.00 mg |
| (4) Hydroxypropyl cellulose | 2.00 mg |
| (5) Light silicic acid anhydride | 1.50 mg |
| (6) Magnesium stearate | 2.00 mg |
| Total | 200 mg |

(1)+(2)+(3) was kneaded with a 5% aqueous solution of (4), granulated, and mixed with (5) and (6). The resultant mixture was filled in No. 3 hard capsules (200 mg/capsule).

In the above Examples 21 and 22, "active ingredient" shows any one of the compounds of the formula (I').

TEST EXAMPLE 1

Antihyaluronidase activity

In view of the fact that antiallergic agents such as sodium cromoglicate (DSCG), tranilast, etc. inhibit the hyaluronidase activity and that compounds which release histamine from the mast cells such as the compound 84/80 and polymixin B activate the hyaluronidase, it is considered that the hyaluronidase inhibiting activity can be taken as an index for the antiallergic action. [cf. The 5th Medicinal Chemistry Symposium (Dec. 9 and 10, 1983; Kyoto) Synopsis of Lectures, page 68]. On the basis of such knowledge, the compounds according to the invention were tested for antihyaluronidase activity and found to have the excellent activities.

TEST METHOD

A buffer solution of hyaluronidase (0.1 ml) was taken in a test tube and buffer solutions of various compounds in various concentrations (0.2 ml each) were added. The mixture was incubated at 37° C. for 20 minutes. Then, a buffer solution of activating agent (Compound 48/80 or CaCl$_2$) (0.2 ml) was added up to the total volume of 0.5 ml, and the mixture was incubated at 37° C. for 20 minutes. To this solution, potassium hyaluronate buffer solution (0.5 ml) was added and the mixture was incubated at 37° C. for 40 minutes. After cooling, the solution was neutralized with 0.4N aqueous solution of sodium hydroxide (0.2 ml) to stop the reaction. On the resulting solution, OD$_{585}$ was determined by modified Morgan-Elson method. A buffer solution or water (0.2 ml) was used as a control in place of the solution of the compounds in the same operation including OD$_{585}$ measurement. (Final concentration of hyaluronidase was 340 NF unit/ml.)

$$\text{Inhibition rate} = \frac{(\text{Control OD}_{585} - \text{Sample OD}_{585})}{\text{Control OD}_{585}} \times 100$$

(Results)

| Compound | IC$_{50}$ (mM) |
|---|---|
| 1 | 0.086 |
| 2 | 0.140 |
| 3 | 0.160 |
| 4 | 0.258 |
| 5 | 0.300 |
| 6 | 0.120 |

It can be seen from the table that all the tested compounds have hyaluronidase inhibiting activity.

TEST EXAMPLE 2

Anti-SRS-A Action

Method of Preparing Crude SRS-A Solution

A piece of lung of guinea pig sensitized with ovalbumin was incubated with antigen ovalbumin at 37° C. for 20 minutes and supernatant was separated in order to use as a crude SRS-A solution.

Determinaiton of Anti-SRS-A Reaction

A piece of ileum of a normal guinea pig was suspended in Tyrode's solution in a Magnus tube and incubated with a solution of the compound to be tested for a predetermined duration. The contraction of the piece of ileum induced by adding the above crude SRS-A solution was compared with that attributed to 10$^{-6}$M histamine dihydrochloride (which was taken as 100). The anti-SRS-A action was shown in terms of the rate of inhibition to the contraction.

Results

The compound 1 showed 14.8% inhibition at $10^{-4}$M and 23.9% inhibition at $10^{-3}$M. The compound 2 showed 11.0% inhibition at $10^{-3}$M. Thus, both the compounds showed mild anti-SRS-A action. To the contrary, tranilast used as a control showed no action.

TEST EXAMPLE 3

Anti-Schultz-Dale Action

Determination of anti-Schultz-Dale reaction

A piece of ileum of guinea pig active-sensitized with ovalbumin with Freund complete adjuvant was suspended in Tyrode's solution in a Magnus tube and incubated with a solution of the compound to be tested for a predetermined duration. The contraction of the piece of ileum induced by applying the ovalubumin was compared with that attributed to $10^{-6}$M histamine dihydrochloride. The anti-Schultz-Dale action was shown in terms of the rate of inhibition to the contraction.

The compound 1 showed 83.5% inhibition at $10^{-3}$M, and the compound 2 100% inhibition at $10^{-3}$M. Both compounds showed a strong anti-Schultz-Dale action at $10^{-3}$M. To the contrary, Tranilast which was used as control showed no action.

TEST EXAMPLE 4

Activity of Inhibition of Histamine Release From Mast Cell in Abdominal Cavity of Rats.

Examination was made on the activity of inhibition of histamine release from mast cell by antigen-antibody reaction.

Preparing of DNP-Ascaris anti-serum

Swine ascaris extract solution was dinitrophenylated according to Aisen's method, dialysed, and lyophilized. The product was administered as antigen together with Bordetella Pertussis vaccine subcutaneously into the foot pad of rat. Eight days later, blood was taken in order to obtain antiserum. The PCA titer for this antiserum in rat was 32 to 64.

Method of collecting mast cell in abdominal cavity and sensitizing cell

Heparin-containing PBS was injected intraperitoneally to rat which was sacrificed by exsanguination, after which the abdomen was well massaged. Then the injected PBS was collected and purified by washing several times by centrifugation. The number of the mast cells contained in the solution was determined and adjusted to the designed concentration. As to method of sensitizing the cell, the above cell suspension (6 ml, $2 \times 10^6$ cells/ml) was treated with anti-DNP-Ascaris rat serum (PCA titer 32) (6 ml) and the mixture was incubated in the presence of heparin at 37° C. for 2 hours.

Quantitative determination of released histamine

To the sensitized mast cell suspension, the solution of the compound to be tested was added, and the mixture was preliminarily incubated at 37° C. for 12 minutes. After addition of the solution of antigen DNP-Ascaris (final concentration: 20 microgramms/ml), the mixture was further incubated for 20 minutes. After completion of the reaction, the solution was centrifuged (500 G, 10 min.) at a low temperature to obtain a supernatant solution. Histamine contained in the supernatant solution was determined by fluorometry using orthophthalaldehyde method.

Results

Amount of histamine released from peritoneal mast cell (Control=100):

| Compound | $10^{-6}$ | $10^{-5}$ | $10^{-4}$ | $10^{-3}$ (M) |
|---|---|---|---|---|
| Tranilast | 95 | 95 | 67 | 29 |
| 1 | 31 | 36 | 11 | −88 |
| 2 | 11 | 24 | −70 | −130 |
| 3 | 95 | 85 | 36 | 0 |

Final concentration of DNP-Ascaris (antigen): 20 microgramms/ml

The compounds 1 and 2 showed the action of inhibiting release of histamine from the mast cell even at the low concentration of $10^{-6}$M. Both inhibited natural release of histamine at $10^{-3}$M. The compound 3 showed strong inhibition from $10^{-4}$M. All three compounds showed the stronger inhibitory activity than the control tranilast in the range of $10^{-6}$M to $10^{-3}$M.

TEST EXAMPLE 5

Anti-Passive Cutaneous Anaphylaxis (PCA) Activity in Rats

Test method

Wistar strain rats were sensitized with ovalbumin using aluminium hydroxide gel and Bordetella Pertussis vaccine as adjuvants. Dilutions of antiserum (16-fold and 32-fold) obtained by collecting blood samples 14 days later were administered subcutaneously in the dorsal skin of the rats of the same strain at the rate of 0.1 ml per spot, and the rats were grown for 48 hours. One hour after peroral administration of the sample solution, a mixture of antigen ovalbumin and Evans-blue dye was administered to the tail venous of the animal according to the ordinary procedure. Thirty minutes later, the animals were sacrificed by exsanguination, and the areas of blue spots (long diameter × short diameter) eliciting on the portion of the antiserum injection at the dorsal skin were measured to obtain the rate of inhibition based on the average value shown by the control animals.

Results

Anti-PCA activity

| Com-pound | Dose mg/kg | route | (N) | Average Inhibition Rate (%) | |
|---|---|---|---|---|---|
| | | | | Antiserum Dilution: × 16 | Antiserum Dilution: × 32 |
| Control | — | PO | 10 | 0 | 0 |
| 1 | 100 | PO | 10 | 31.6 | 41.8 |
| 2 | 100 | PO | 10 | 26.7 | 21.2 |

The compound 2 and 3 showed the anti-PCA activity.

TEST EXAMPLE 6

Acute Toxicity

Test method

As test animals, ddy-strain mice (male) were used. According to the conventional procedure, suspension or solution of test compound was administered to the animals. From the number of the dead animals up to one week after the administration, $LD_{50}$ values were obtained by Provit method.

Results

| Compound | LD50 (mg/kg of body weight) mice | |
|---|---|---|
| | PO | Intravenous |
| 1 | 615.0 | 437.7 |
| 2 | 399.8 | 277.4 |

What is claimed is:

1. A compound of the formula:

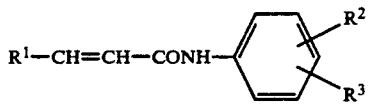

wherein $R^1$ is a five-membered heterocyclic group containing one or two heteroatoms selected from nitrogen and sulfur and which is unsubstituted or substituted with lower alkyl or lower alkoxycarbonyl, $R^2$ is hydrogen, and $R^3$ is a carboxy group or an ester thereof, with the proviso that when $R^1$ is an unsubstitued or substituted thienyl, then $R^3$ is attached to the ortho position with respect to —CONH—, and, where applicable pharmaceutically acceptable salts thereof.

2. The compound according to claim 1, wherein $R^3$ is attached at ortho position in respect to —CONH—.

3. The compound according to claim 1, wherein $R^1$ is a heterocyclic group having at least one —S—, —NH— or —NY— wherein Y is lower alkyl or lower alkoxycarbonyl.

4. The compound according to claim 1, wherein $R^1$ is a heterocyclic group selected from the group consisting of 2-thienyl, 3-thienyl, 1-methyl-2-pyrrolyl and 4-imidazolyl.

5. The compound according to claim 1, wherein $R^3$ is physiologically hydrolyzable ester.

6. A pharmaceutical composition useful as a hyaluronidase inhibitor comprising as an active ingredient a compound of the formula:

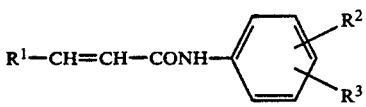

wherein $R^1$ is a five-membered heterocyclic group containing one or two hetero atoms selected from nitrogen and sulfur and which is unsubstituted or substituted with lower alkyl or lower alkoxycarbonyl, $R^2$ is hydrogen, and $R^3$ is carboxy or an ester thereof with the proviso that when $R^1$ is an unsubstituted or substituted thienyl, then $R^3$ is attached to the ortho position with respect to —CONH— or, where applicable, pharmaceutically acceptable salts thereof in association with a pharmaceutically acceptable carrier, diluent or excipient.

7. A pharmaceutical composition useful for treating allergic disease in mammals comprising a compound of the formula:

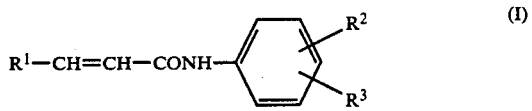

wherein $R^1$ is a five-membered heterocyclic group containing one or two hetero atoms selected from nitrogen and sulfur and which is unsubstituted or substituted with lower alkyl or lower alkoxycarbonyl, $R^2$ is hydrogen, and $R^3$ is carboxy group or an ester thereof, with the proviso that when $R^1$ is an unsubstitued or substituted thienyl, then $R^3$ is attached to the ortho position with respect to —CONH— or, where applicable, pharmaceutically acceptable salts thereof in association with a pharmaceutically acceptable carrier, diluent or excipient.

8. The compound according to claim 1 wherein said ester is selected from the group consisting of lower alkyl ester, lower alkenyl ester, lower alkynyl ester, lower alkoxy (lower)alkyl ester, lower alkylthio(lower)alkyl ester, halo(lower)alkyl ester, lower alkanesulfonyl(lower)alkyl ester, aryl ester, aryl(lower)alkyl ester, tri(lower)alkylsily ester, di(lower)alkyl(lower)alkoxysilyl ester, acetoxy methyl ester, 1-(ethoxycarbonyloxy) ethyl ester, pivaloyloxymethyl ester, phthalidyl ester, 5-indanyl ester, 2-(3-phthalidylidene)ethyl ester, and (5-methyl-2-oxo-1,3-diaxole-4-yl)methyl ester.

9. The compound according to claim 8 wherein aryl is phenyl.

10. The compound according to claim 1 which is 2-[3-(3-thienyl)] acrylamidobenzoic acid, 2-[3-(2-thienyl)] acrylamidobenzoic acid or 2-[3-(1-methyl-2-pyrrolyl)] acrylamidobenzoic acid.

11. The composition according to claim 6 wherein said ester is selected from the group consisting of lower alkyl ester, lower alkenyl ester, lower alkynyl ester, lower alkoxy (lower) alkyl ester, lower alkylthio(lower)alkyl ester, halo (lower)alkyl ester, lower alkanesulfonyl(lower)alkyl ester, aryl ester, aryl(lower)alkyl ester, tri(lower)alkylsilyl ester, di(lower)alkyl(lower)alkoxysilyl ester, acetoxy methyl ester, 1-(ethoxycarbonyloxy)ethyl ester, pivaloyloxymethyl ester, phthalidyl ester, 5-indanyl ester, 2-(3-phthalidylidene) ethyl ester, and (5-methyl-2-oxo-1,3-diaxole-4-yl)methyl ester.

12. The composition according to claim 13 wherein aryl is phenyl.

13. The composition according to claim 7 wherein said ester is selected from the group consisting of lower alkyl ester, lower alkenyl ester, lower alkynyl ester, lower alkoxy (lower)alkyl ester, lower alkylthio(lower)alkyl ester, halo (lower)alkyl ester, lower alkanesulfonyl(lower)alkyl ester, aryl ester, aryl(lower)alkyl ester, tri(lower)alkylsilyl ester, di(lower)alkyl(lower)alkoxysilyl ester, acetoxy methyl ester, 1-(ethoxycarbonyloxy) ethyl ester, pivaloyloxymethyl ester, phthalidyl ester, 5-indanyl ester, 2-(3-phthalidylidene) ethyl ester, and (5-methyl-2-oxo-1,3-diaxole-4-yl) methyl ester.

14. The composition according to claim 13 wherein aryl is phenyl.

* * * * *

UNITED STATES PATENT AND TRADEMARK OFFICE
CERTIFICATE OF CORRECTION

PATENT NO. : 5,006,548

DATED : April 9, 1991

INVENTOR(S) : Yoshifumi Kanamoto, et al.

It is certified that error appears in the above-identified patent and that said Letters Patent is hereby corrected as shown below:

Column 16, line 9: "84/80" should read as --48/80--

Signed and Sealed this

Fifteenth Day of December, 1992

Attest:

DOUGLAS B. COMER

Attesting Officer

Acting Commissioner of Patents and Trademarks